United States Patent
Koka et al.

(10) Patent No.: US 11,317,842 B2
(45) Date of Patent: *May 3, 2022

(54) SYSTEMS AND METHODS FOR SELF-FITTING AN ELECTROACOUSTIC STIMULATION SYSTEM TO A PATIENT

(71) Applicant: Advanced Bionics AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

( * ) Notice: Subject to any disclaimer, the term of this patent is extended or adjusted under 35 U.S.C. 154(b) by 213 days.

This patent is subject to a terminal disclaimer.

(21) Appl. No.: 16/775,896

(22) Filed: Jan. 29, 2020

(65) Prior Publication Data

US 2020/0169820 A1    May 28, 2020

Related U.S. Application Data

(63) Continuation of application No. 15/515,553, filed as application No. PCT/US2014/059341 on Oct. 6, 2014, now Pat. No. 10,560,789.

(51) Int. Cl.
*H04R 25/00* (2006.01)
*A61B 5/04* (2006.01)
(Continued)

(52) U.S. Cl.
CPC ............... *A61B 5/24* (2021.01); *A61B 5/121* (2013.01); *A61B 5/125* (2013.01); *A61N 1/0541* (2013.01);
(Continued)

(58) Field of Classification Search
CPC .. H04R 25/505; H04R 25/70; H04R 2225/67; A61N 1/36036; A61N 1/0541; A61B 5/125; A61B 5/04001; A61B 5/121
See application file for complete search history.

(56) References Cited

U.S. PATENT DOCUMENTS 8,086,319 B2    12/2011    Van Dijk
8,644,535 B2    2/2014    Steinbuss
(Continued)

FOREIGN PATENT DOCUMENTS

WO    2012056427    5/2012
WO    2013142843    9/2013
(Continued)

OTHER PUBLICATIONS

International Search Report and Written Opinion received in International Application No. PCT/US14/059341, dated Mar. 6, 2015.
(Continued)

*Primary Examiner* — Mark W. Bockelman
(74) *Attorney, Agent, or Firm* — ALG Intellectual Property, LLC

(57) ABSTRACT

An exemplary system includes an electro-acoustic stimulation ("EAS") sound processor, a cochlear implant communicatively coupled to the EAS sound processor, an electrode array communicatively coupled to the cochlear implant, and a receiver communicatively coupled to the EAS sound processor and configured to be in communication with an ear of a patient. The EAS sound processor 1) directs, while in a self-fitting mode, the receiver to apply acoustic stimulation to the patient, 2) records, using at least one electrode included in the electrode array, an evoked response that occurs in response to the acoustic stimulation, 3) compares the evoked response to a baseline evoked response recorded by the EAS sound processor prior to recording the evoked response, and 4) performs a predetermined action based on the comparison between the evoked response and the baseline evoked response. Corresponding systems and methods are also disclosed.

20 Claims, 10 Drawing Sheets

(51) Int. Cl.
    *A61B 5/12*           (2006.01)
    *A61N 1/36*           (2006.01)
    *A61B 5/24*           (2021.01)
    *A61N 1/05*           (2006.01)

(52) U.S. Cl.
    CPC ....... *A61N 1/36039* (2017.08); *H04R 25/505* (2013.01); *H04R 25/70* (2013.01); *H04R 2225/67* (2013.01)

(56) References Cited

U.S. PATENT DOCUMENTS

| | | |
|---|---|---|
| 9,179,231 B2 | 11/2015 | Johnston et al. |
| 2012/0300964 A1 | 11/2012 | Ku et al. |
| 2013/0006328 A1 | 1/2013 | Bouchataoui et al. |

FOREIGN PATENT DOCUMENTS

| | | |
|---|---|---|
| WO | 2013142844 | 9/2013 |
| WO | 2013142846 | 9/2013 |
| WO | 2017182931 | 10/2017 |

OTHER PUBLICATIONS

Non-Final Office Action received in U.S. Appl. No. 15/515,553 dated Apr. 5, 2019.

SYSTEMS AND METHODS FOR SELF-FITTING AN ELECTROACOUSTIC STIMULATION SYSTEM TO A PATIENT

RELATED APPLICATIONS

The present application is a continuation application of U.S. patent application Ser. No. 15/515,553, filed Oct. 6, 2014, which application is a U.S. National Stage Entry of PCT Application No. PCT/US14/59341, filed Oct. 6, 2014. The contents of these applications are incorporated herein by reference in their respective entireties.

BACKGROUND INFORMATION

Many hearing loss patients have some degree of residual hearing in the low frequencies (e.g., below 1 kHz) and a severe hearing loss in the high frequencies (e.g., above 1 kHz). These people cannot benefit from traditional hearing aid amplification because of the severity of the hearing loss in the high frequencies. Nor are they classic cochlear implant candidates, because of their mostly intact low frequency residual hearing.

For this group of people, electro-acoustic stimulation ("EAS") systems have been developed that provide such patients with the ability to perceive both low and high frequencies. Electro-acoustic stimulation combines the functionality of a hearing aid and a cochlear implant together in the same ear by providing acoustic stimulation representative of low frequency audio content and electrical stimulation representative of high frequency content. The auditory nerve combines the acoustic and electric stimuli into one auditory signal. Results of various studies have shown that electro-acoustic stimulation may enhance speech understanding, pitch discrimination, and music appreciation.

The effectiveness of an EAS system may be affected by a number of different factors. For example, surgical complications (e.g., a misalignment of an electrode array within the cochlea, destruction of hair cells during implantation of a cochlear implant, etc.) and post-surgery complications (e.g., residual hearing loss, wax buildup in the ear, infections, and component failure) may be detrimental to EAS system performance. Unfortunately, many of these factors are not readily discernible, thereby making it difficult or impossible to account for them (e.g., by adjusting one or more control parameters governing an operation of the EAS system). Hence, a patient may unknowingly suffer from sub-optimal EAS system performance.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
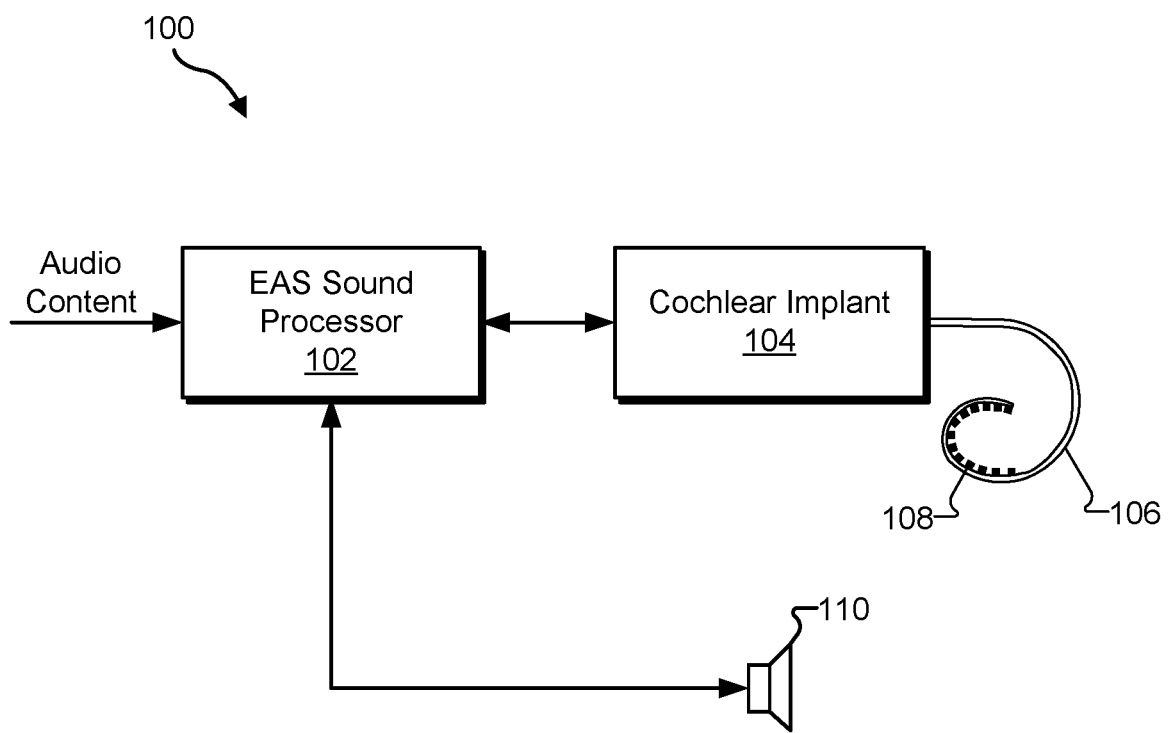
FIG. 1 illustrates an exemplary EAS system according to principles described herein.

Systems and methods for self-fitting an EAS system to a patient are described herein. As will be described below, an exemplary EAS system may include an electro-acoustic stimulation ("EAS") sound processor configured to be located external to a patient, a cochlear implant communicatively coupled to the EAS sound processor and configured to be implanted within the patient, an electrode array communicatively coupled to the cochlear implant and configured to be located within a cochlea of the patient, and a receiver communicatively coupled to the EAS sound processor and configured to be in communication with an ear of the patient. In certain examples, the EAS sound processor 1) directs, while in a self-fitting mode, the receiver to apply acoustic stimulation to the patient, 2) records, using at least one electrode included in the electrode array, an evoked response that occurs in response to the acoustic stimulation, 3) compares the evoked response to a baseline evoked response recorded by the EAS sound processor prior to recording the evoked response, and 4) performs a predetermined action based on the comparison between the evoked response and the baseline evoked response.

As used herein, an "evoked response" may include any type of cochlear response and/or neural response. Exemplary cochlear responses include, but are not limited to, cochlear microphonics, summating potentials, otoacoustic emissions, intracochlear hair-cell responses, etc. Exemplary neural responses include, but are not limited to, auditory nerve responses (e.g., auditory nerve neurophonics responses, auditory overlapped waveform, etc.), brainstem responses, compound action potentials, frequency following responses, etc. An evoked response may additionally or alternatively include any other type of response that may occur in response to application of electrical and/or acoustic stimulation by an EAS system and that may be recorded using an intracochlear electrode.

As used herein, a "self-fitting mode" refers to a mode of operation of the EAS sound processor in which the EAS sound processor performs one or more self-fitting operations. While in the self-fitting mode, the EAS sound processor does not direct the cochlear implant and/or receiver to apply, to the patient, electrical and/or acoustic stimulation representative of audio signals (e.g., speech and/or other types of sound) presented to the patient. The EAS sound processor may enter the self-fitting mode in any suitable manner, at any suitable time, and for any suitable purpose. In certain examples, the EAS sound processor may enter the self-fitting mode periodically at predetermined intervals or randomly at different times during a given time period (e.g., during a day, a week, a month, a year, etc.). Additionally or alternatively, the EAS sound processor may enter the self-fitting mode in response to a specific instruction provided by the patient, a clinician, and/or any other component (e.g., a fitting device/system).

For example, the EAS sound processor, while in the self-fitting mode, may direct the receiver to apply acoustic stimulation to the patient. The EAS sound processor may then record an evoked response that occurs in response to the acoustic stimulation and compare the evoked response to a baseline evoked response and/or one or more previously recorded evoked responses. If the evoked response differs from the baseline evoked response and/or the one or more previously recorded evoked responses (e.g., if the evoked response is not within a predetermined range of the baseline evoked response and/or the one or more previously recorded evoked responses), the EAS sound processor may set one or more control parameters associated with an acoustic stimulation functionality of the EAS sound processor, determine a degree of amplification to be used for future acoustic stimulation to be provided by the system, determine an optimal crossover frequency associated with the patient, and/or take any other suitable action as may serve a particular implementation. These and other examples will be described in more detail below.

In some instances, as will be described below, the EAS sound processor may switch from the self-fitting mode to a normal stimulation mode. As used herein, a "normal stimulation mode" refers to a mode of operation of the EAS sound processor in which the EAS sound processor processes audio signals presented to the patient and directs the cochlear implant and/or receiver to apply electrical and/or acoustic stimulation representative of the audio signals to the patient. During the normal stimulation mode, the EAS sound processor does not perform self-fitting operations.

After a certain amount of time of operating in the normal stimulation mode, the EAS sound processor may switch from the normal stimulation mode back to the self-fitting mode. While again in the self-fitting mode, the EAS sound processor may again elicit and record an evoked response, compare the newly recorded evoked response with the evoked response recorded while the EAS sound processor was previously in the self-fitting mode, and perform another predetermined action (e.g., adjust one or more control parameters associated with the acoustic stimulation functionality of the EAS sound processor) based on the comparison.

By eliciting an evoked response and then performing a predetermined action based on a comparison between the evoked response and a previously recorded evoked response (e.g., a baseline evoked response), the systems and methods described herein may facilitate self-fitting by the EAS system to the patient. This may improve EAS system performance without requiring the patient to visit a clinic, assist in evaluating one or more conditions (e.g., a residual hearing status) of the patient, and/or otherwise provide benefit to the patient. These and/or additional or alternative benefits and/or advantages that may be provided by systems and methods described herein will be made apparent by the following description. Exemplary systems and methods for self-fitting an EAS system to a patient will now be described in reference to the accompanying drawings.

FIG. 1 illustrates an exemplary EAS system 100. As shown, EAS system 100 may include an EAS sound processor 102, a cochlear implant 104, an electrode array 106 (also referred to as an electrode lead) having a plurality of electrodes 108 disposed thereon, and a receiver 110 (also referred to as a loudspeaker).

EAS sound processor 102 may include any suitable device configured to process audio content (e.g., one or more audio signals) presented to a patient and provide electrical and/or acoustic stimulation representative of the audio signals to the patient. In some examples, EAS sound processor may include or be implemented by a behind-the-ear ("BTE") unit, a body worn device, and/or any other sound processing unit as may serve a particular implementation.

As mentioned, EAS sound processor 102 may be used when the patient has some residual some hearing in the low frequencies (e.g., below 1000 Hz) and severe hearing loss in the high frequencies (e.g., above 1000 Hz). To this end, EAS sound processor 102 may direct cochlear implant 104 to apply electrical stimulation representative of audio content included in a relatively high frequency band (e.g., above 1000 Hz) to one or more stimulation sites within the patient by way of one or more of electrodes 108 and receiver 110 to apply acoustic stimulation representative of audio content included in a relatively low frequency band (e.g., below 1000 Hz) to the patient.

Cochlear implant 104 may include any suitable auditory prosthesis configured to be at least partially implanted within a patient as may serve a particular implementation. For example, cochlear implant 104 may include an implantable cochlear stimulator, a brainstem implant and/or any other type of auditory prosthesis. EAS sound processor 102 and cochlear implant 104 may communicate by way of any suitable wired or wireless communication channel.

Electrode array 106 may be implanted within the patient such that electrodes 108 are in communication with stimulation sites within the cochlea. In this configuration, EAS sound processor 102 may direct cochlear implant 104 to apply electrical stimulation representative of an audio signal to one or more stimulation sites within the patient by way of one or more of electrodes 108. As used herein, the term "in communication with" refers to electrodes 108 being adjacent to, in the general vicinity of, in close proximity to, directly next to, or directly on the one or more stimulation sites. Any number of electrodes 108 (e.g., sixteen) may be disposed on array 106 as may serve a particular implementation.

Figure 2:
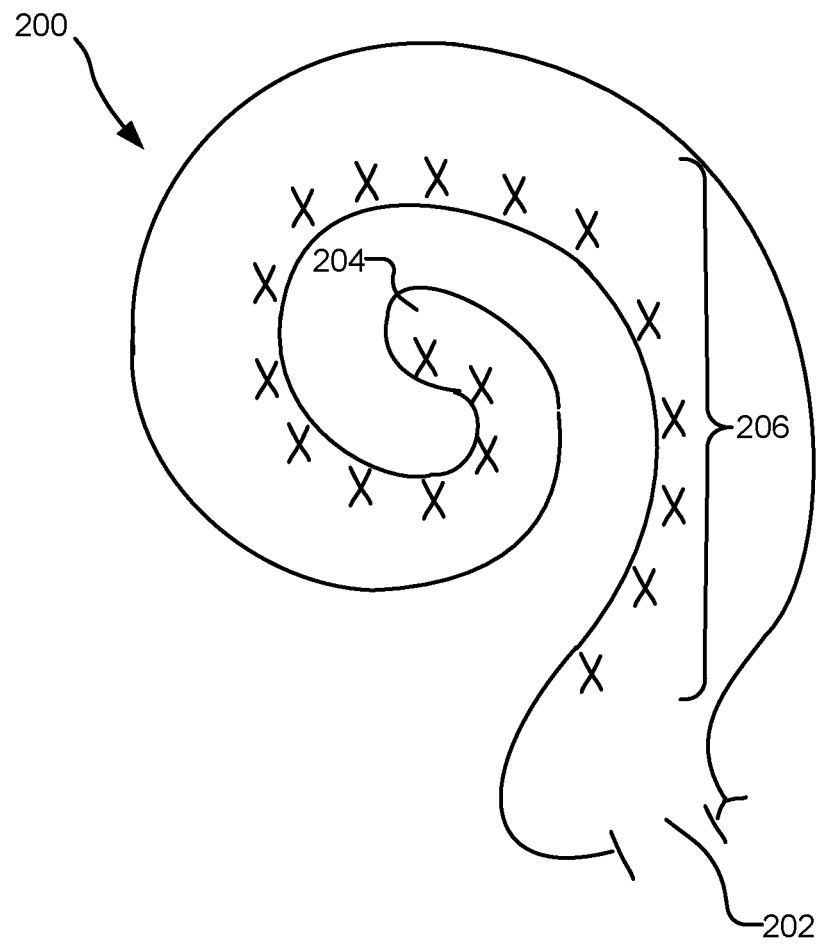
FIG. 2 illustrates a schematic structure of the human cochlea according to principles described herein.

FIG. 2 illustrates a schematic structure of the human cochlea 200 into which electrode array 106 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the lead, the anatomy of the patient's cochlea, and/or any other factor as may serve a particular implementation.

Returning to FIG. 1, receiver 110 may be communicatively coupled to EAS sound processor 102 and may be configured to be in communication with an ear of the patient. For example, receiver 110 may be integrated into an earmold configured to be located within the outer ear of the patient.

The earmold may include any type of earmold that may be at least partially disposed within the outer ear of the patient. For example, the earmold may include an open dome configured to allow the ear to remain partially open (e.g., an open dome tip made from a soft silicone material and configured to resemble a tulip or flower bud), a closed dome configured to entirely close off the ear canal, a foam dome, and/or any other type of dome as may serve a particular implementation. As will be described in more detail below, receiver 110 may be configured to apply acoustic stimulation to the patient.

EAS sound processor 102 may include one or more components that may be external to the patient and may be configured to direct cochlear implant 104 to generate and apply electrical stimulation (also referred to herein as "stimulation current") representative of one or more audio signals (e.g., one or more audio signals detected by a microphone, input by way of an auxiliary audio input port, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, EAS sound processor 102 may process the one or more audio signals in accordance with a selected sound processing strategy or program to generate appropriate stimulation parameters for controlling cochlear implant 104.

In some examples, EAS sound processor 102 may wirelessly transmit stimulation parameters (e.g., in the form of data words included in a forward telemetry sequence) and/or power signals to cochlear implant 104 by way of a wireless communication link between a headpiece and cochlear implant 104. It will be understood that the communication link may include a bi-directional communication link and/or one or more dedicated uni-directional communication links.

EAS sound processor 102 may be further configured to direct receiver 110 to apply acoustic stimulation representative of audio content to the patient. This may be performed in any suitable manner.

Figure 3:
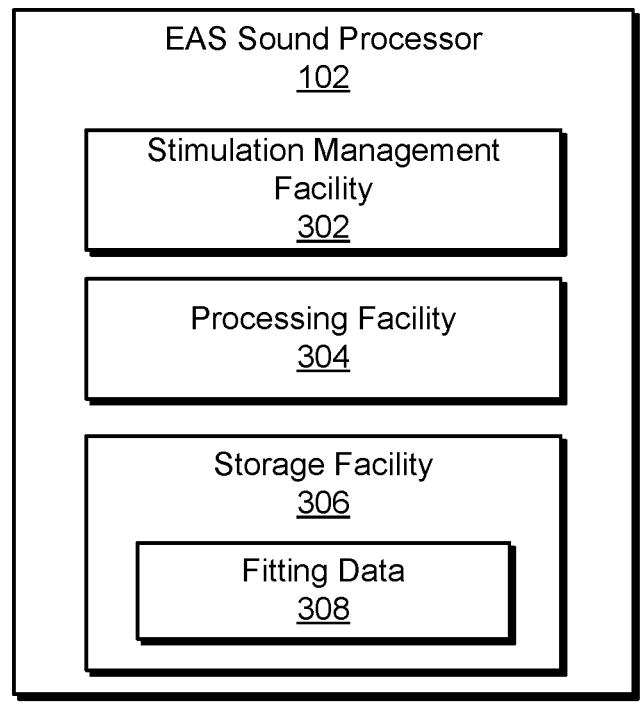
FIG. 3 illustrates exemplary components of an EAS sound processor that is implemented in the system of FIG. 1 according to principles described herein.

FIG. 3 illustrates exemplary components of EAS sound processor 102 that may be incorporated into or otherwise associated with EAS sound processor 102. As shown in FIG. 3, EAS sound processor 102 may include a stimulation management facility 302, a processing facility 304, and a storage facility 306, which may be in communication with one another using any suitable communication technologies. One or more of facilities 302-306 may include one or more computing devices and/or processors configured to perform one or more of the functions described herein. Facilities 302-306 will now be described in more detail.

Stimulation management facility 302 may perform one or more management operations. For example, stimulation management facility 302 may attempt to elicit an evoked response within a patient. This may be performed in any suitable manner. For example, stimulation management facility 302 may direct cochlear implant 104 and/or receiver 110 to apply stimulation to the patient and then determine whether an evoked response occurs in response to the stimulation. The presence or absence of an evoked response may be indicative of one or more conditions (e.g., a residual hearing status of the patient, auditory neuropathy, etc.).

Stimulation management facility 302 may direct cochlear implant 104 and/or receiver 110 to apply stimulation to the patient in any suitable manner. For example, stimulation management facility 302 may direct cochlear implant 104 to apply electrical stimulation to the patient by way of at least one electrode 108 included in electrode array 106. The electrical stimulation may have any suitable characteristic. For example, the electrical stimulation may include monopolar stimulation. The electrode to which the electrical stimulation is applied may be any electrode located within the cochlea of the patient (e.g., the most apical electrode included in electrode array 106).

As another example, stimulation management facility 302 may direct receiver 110 to apply acoustic stimulation to the patient. The acoustic stimulation may have any suitable characteristic as may serve a particular implementation. For example, the acoustic stimulation may include a relatively low frequency tone burst (e.g., a 125 Hz tone burst).

As another example, stimulation management facility 302 may direct cochlear implant 104 and receiver 110 to concurrently apply electrical stimulation and acoustic stimulation to the patient.

Processing facility 304 may be perform one or more processing operations associated with EAS system 100. For example, if stimulation management facility 302 directs receiver 110 to apply acoustic stimulation to the patient while EAS sound processor 102 is in a self-fitting mode, processing facility 304 may perform one or more predetermined actions in accordance with an evoked response that occurs in response to the acoustic stimulation (or in accordance with an evoked response not occurring in response to the acoustic stimulation). Exemplary predetermined actions that may be performed by processing facility 304 will be described in more detail below.

Processing facility 304 may determine whether an evoked response occurs in response to the acoustic stimulation in any suitable manner. For example, stimulation management facility 302 may use one or more electrodes to monitor for and record the evoked response. For example, a cochlear response (e.g., cochlear microphonics) may be recorded using one or more electrodes positioned within the cochlea (e.g., one or more of electrodes 108), one or more electrodes positioned within the round window, and/or one or more electrodes positioned at any other suitable location relatively near the cochlea. Likewise, a neural response (e.g., an auditory nerve response and/or a compound action potential) may be recorded using one or more electrodes positioned within or near the cochlea. It will be recognized that the electrode(s) used to record the evoked response may be disposed on a lead that has been inserted into the cochlea (e.g., electrode array 106), on a fly lead that has been positioned at any other suitable location within the patient, or on any other lead as may serve a particular implementation.

In some examples, one or more electrodes located external to the patient may be used to record an evoked response. For example, a brainstem response may be recorded using one or more non-invasive electrodes that have been affixed externally to the head of the patient.

In some examples, processing facility 304 may use a microphone configured to be located within the ear canal of the patient to detect and record an evoked response (e.g., one or more otoacoustic emissions). These and other exemplary configurations that may be used to record evoked responses will be described in more detail below.

Storage facility 306 may be configured to maintain fitting data 308 generated and/or utilized by stimulation management facility 302 and/or processing facility 304. In some examples, EAS sound processor 102 may store data representative of a baseline evoked response and one or more evoked responses within storage facility 306 as fitting data 308. Storage facility 306 may be configured to maintain additional or alternative data as may serve a particular implementation.

A patient's hearing loss may fluctuate over time due to various factors associated with the patient and EAS system 100. In addition, over time, other factors may affect performance of EAS system 100. Such factors may include wax buildup in the ear, illness (e.g., an infection), component failure, and/or any other factor. Accordingly, once a patient has been provided with EAS system 100, during normal operation of EAS system 100, and/or during follow-up test and checkups thereafter, it may be necessary to re-fit EAS system 100 to the patient. Such "re-fitting" may include EAS sound processor 102 automatically performing a predetermined action to compensate for changes (e.g., changes in a residual hearing status of a patient) that may have occurred after the patient was initially fit with EAS system 100. In this regard, EAS sound processor 102 may be configured to self-fit EAS system 100 to the patient. To facilitate self-fitting of EAS system 100 to a patient, EAS sound processor 102 may enter a self-fitting mode during which EAS sound processor 102 directs receiver 110 to apply acoustic stimulation to the patient. EAS sound processor 102 may direct receiver 110 to apply acoustic stimulation to the patient while in the self-fitting mode in any suitable manner. For example, stimulation management facility 302 may direct receiver 110 to apply acoustic stimulation in the form of an audio tone, an audio tone complex, clicks, etc. In some examples, the acoustic stimulation may be applied in isolation (i.e., in the absence of electrical stimulation).

In certain examples, stimulation management facility 302 may, while in the self-fitting mode, direct receiver 110 to apply acoustic stimulation to the patient in a manner that is sufficient to record cochlear microphonics and auditory nerve neurophonics responses. As discussed above, an evoked response may include, for example, compound action potential responses, cochlear microphonics responses, and auditory nerve neurophonics responses. Compound action potential responses may be measured with relatively shorter duration acoustic stimulations (e.g., clicks, tone pips, etc.) and shorter recordings. However, cochlear microphonics and auditory nerve neurophonics responses may require longer duration acoustic stimulations (e.g., longer tones) and recordings. Accordingly, in certain examples, stimulation management facility 302 may direct receiver 110 to apply the acoustic stimulation to the patient for a duration (e.g., greater than 2ms) that is sufficient to record cochlear microphonics and auditory nerve neurophonics responses as well as compound action potential responses.

Figure 4:
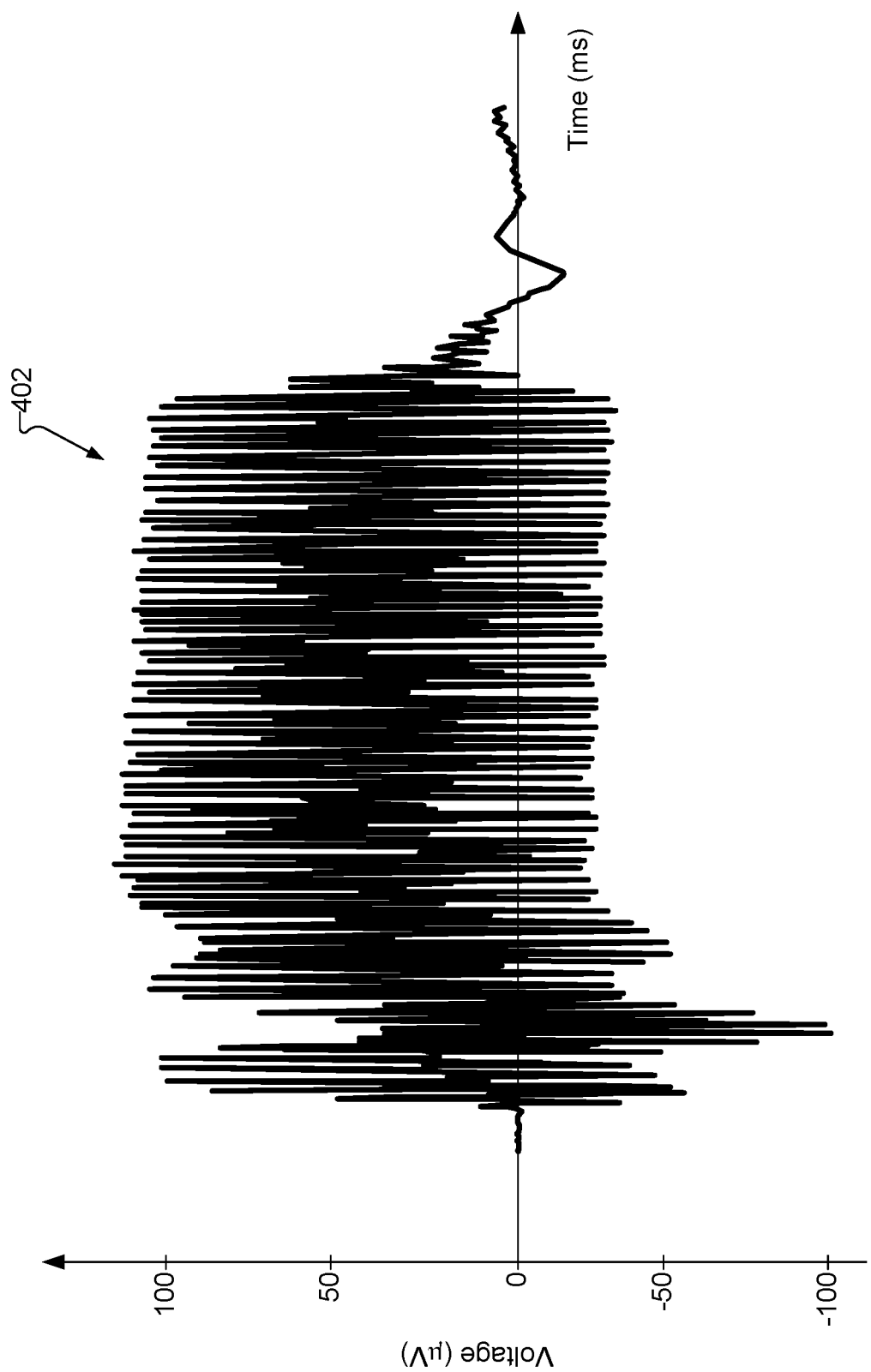
FIG. 4 illustrates an exemplary baseline evoked response that may occur in response to application of acoustic stimulation according to principles described herein.

After receiver 110 applies the acoustic stimulation, processing facility 304 may record an evoked response (e.g., by using at least one electrode 108 included in electrode array 106) that occurs in response to the acoustic stimulation in any suitable manner. In some examples, processing facility 304 may then store data representative of the evoked response as fitting data 308 in storage facility 306. Processing facility 304 may then compare the evoked response, in any suitable manner, to a baseline evoked response and/or one or more previously recorded evoked responses. As used herein, a "baseline evoked response" refers to some type of fixed evoked response that a clinician may consider to be normal, acceptable, and/or desirable. In certain examples, the baseline evoked response may be recorded during an initial fitting procedure and stored by storage facility 306 to be used by EAS sound processor 102 for any suitable purpose. To illustrate, FIG. 4 shows an exemplary baseline evoked response 402 that may occur in response to acoustic stimulation provided by EAS system 100.

As discussed, certain changes may occur after baseline evoked response 402 is recorded that affect the acoustic functionality of EAS system 100. In view of the changes, if the same acoustic stimulation that is used to generate baseline evoked response 402 is applied to the patient at a later time, the acoustic stimulation may result in an evoked response that deviates from the baseline evoked response. This may be indicative of a change in (e.g., a degradation of) acoustic stimulation functionality of EAS sound processor 102.

Accordingly, in certain examples, processing facility 304 may compare an evoked response elicited while EAS sound processor 102 is in a self-fitting mode to baseline evoked response 402. Based on the comparison, processing facility 304 may adjust one or more acoustic stimulation parameters associated with the acoustic stimulation functionality of EAS sound processor 102 and/or perform one or more other predetermined actions.

Processing facility 304 may compare the evoked response to baseline evoked response 402 in any suitable manner. For example, processing facility 304 may compare an amplitude of the evoked response (e.g., an amplitude of the envelope of the evoked response) with an amplitude of baseline evoked response 402.

Figure 5:
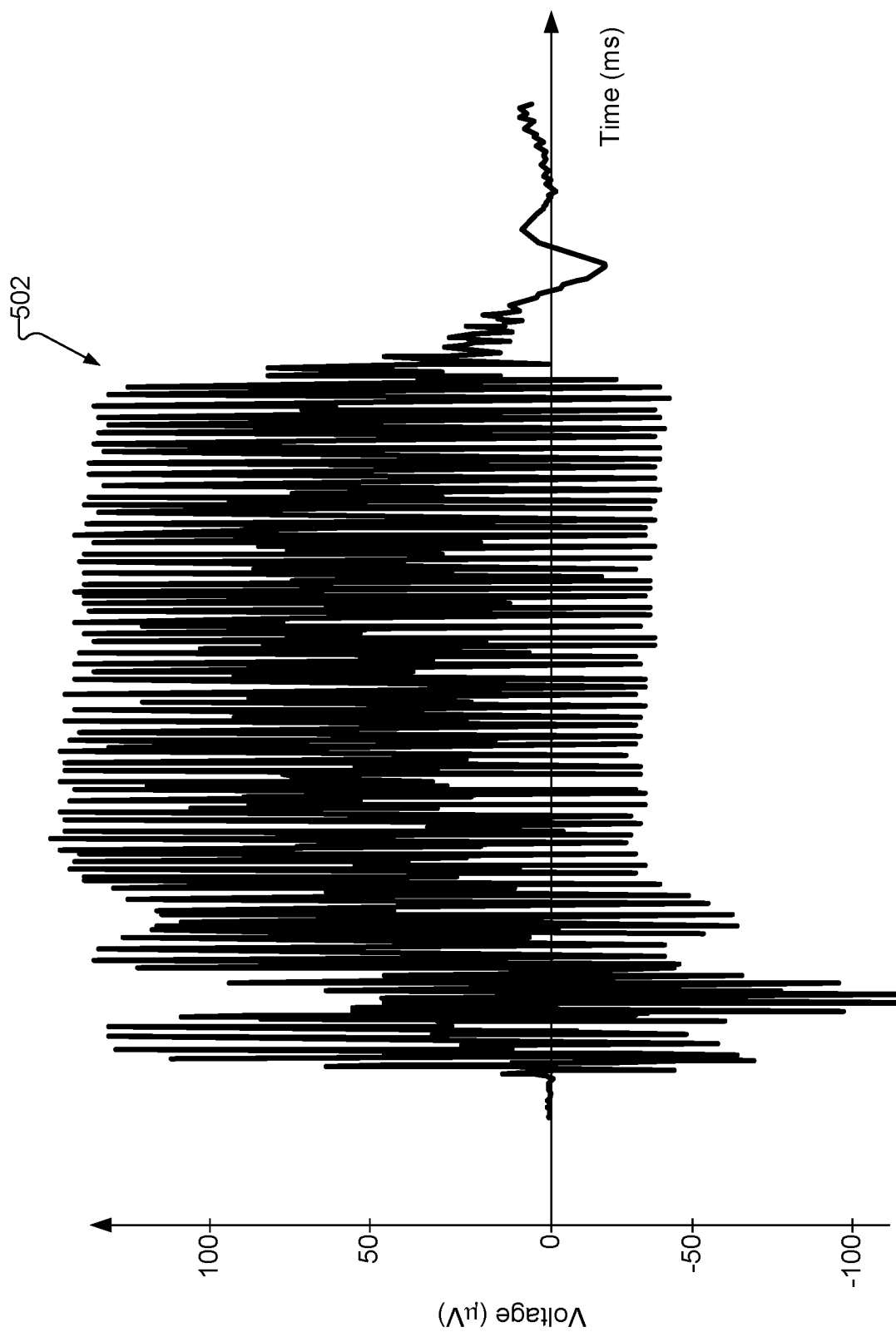
FIGS. 5-7 illustrate exemplary comparisons between an exemplary baseline evoked response and exemplary evoked responses that may occur in response to a subsequent application of acoustic stimulation according to principles described herein.
Figure 6:
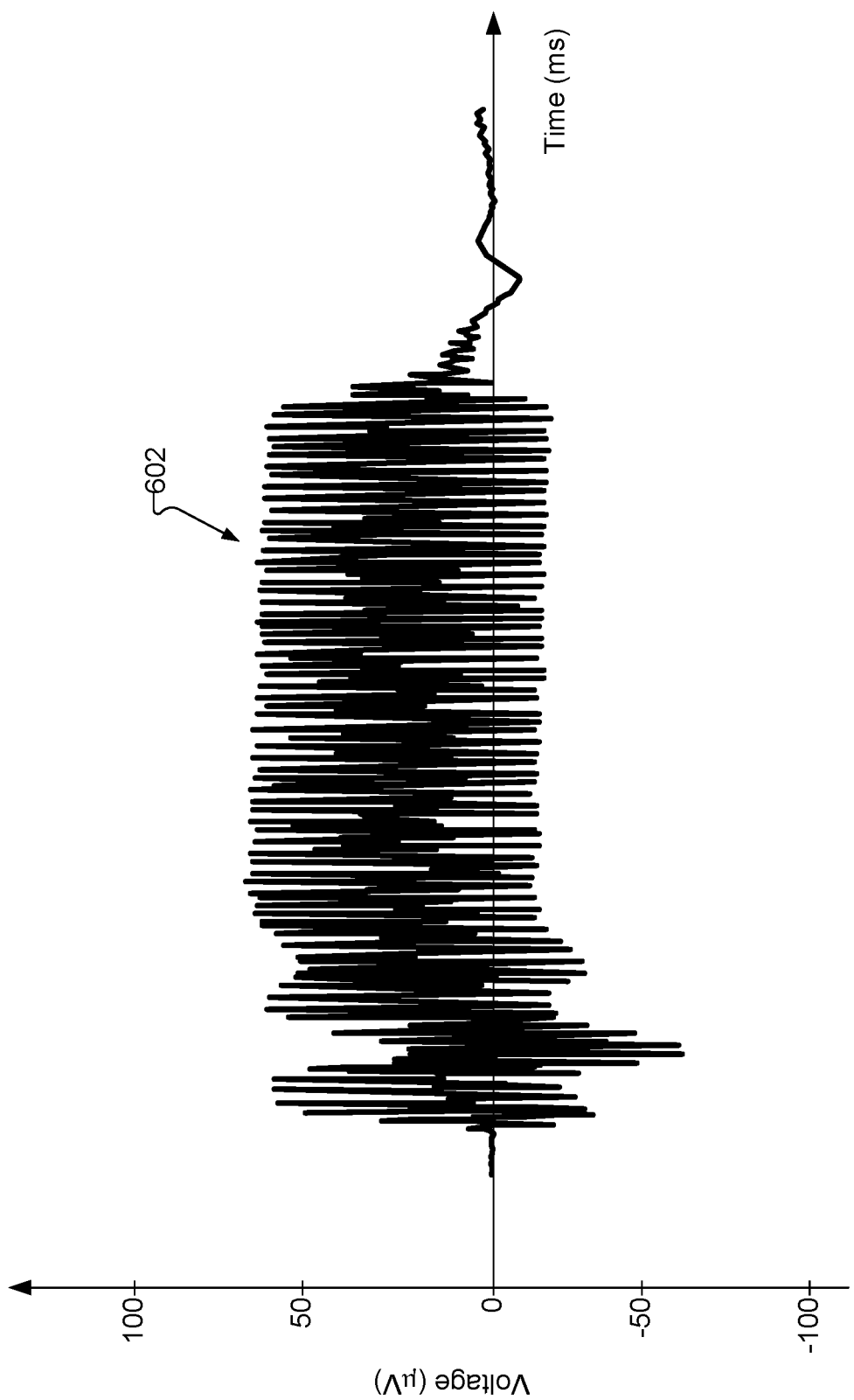
Figure 7:
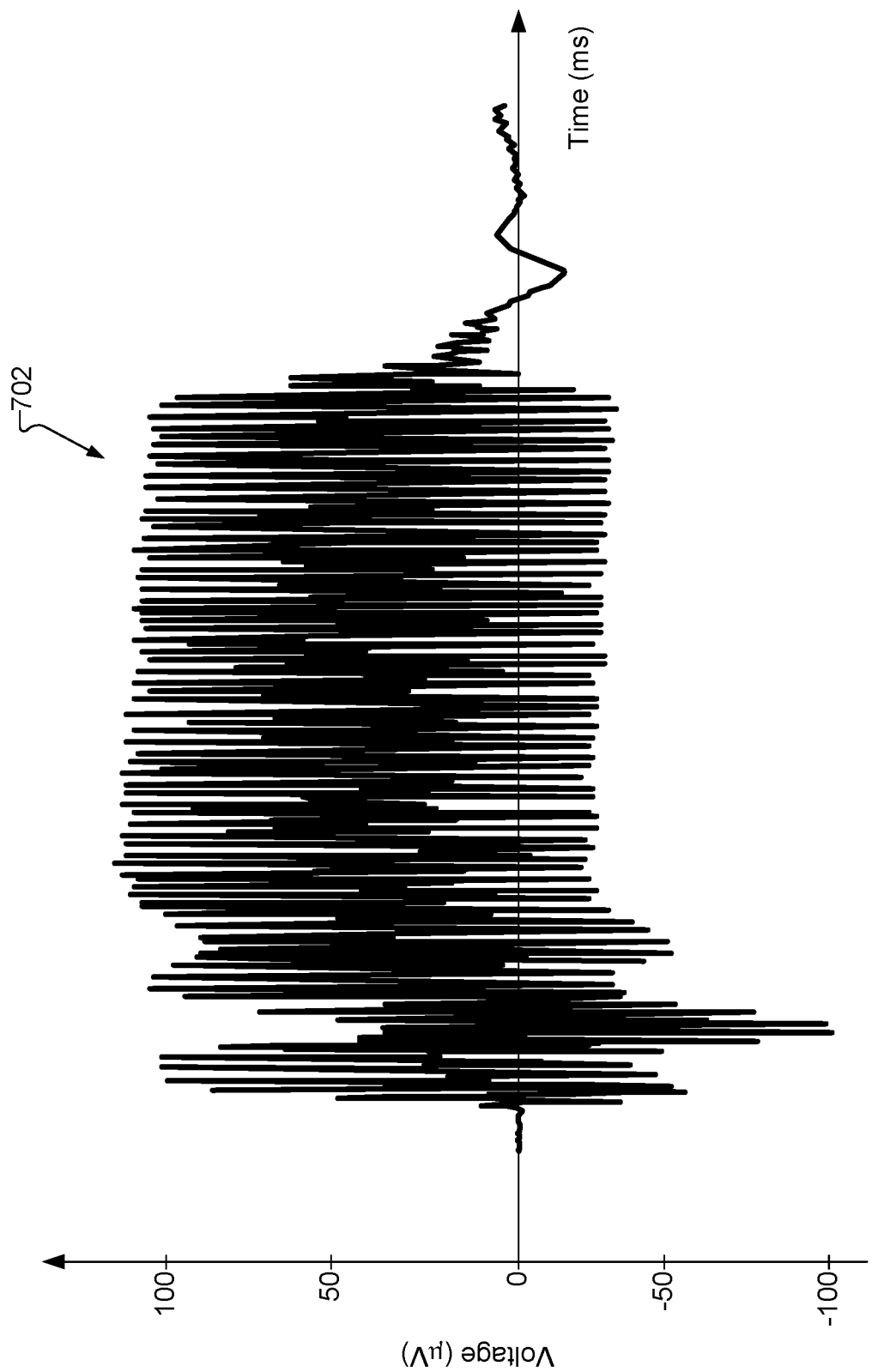

To illustrate, FIGS. 5-7 show exemplary evoked responses 502, 602, and 702 that may occur in response to the same acoustic stimulation used to record baseline evoked response 402 being applied after baseline evoked response 402 is recorded. As shown in FIG. 5, evoked response 502 has an amplitude that is greater than the amplitude of baseline evoked response 402 shown in FIG. 4. Accordingly, processing facility 304 may determine that evoked response 502 is greater than baseline evoked response 402. Conversely, evoked response 602 shown in FIG. 6 has an amplitude that is less than the amplitude of baseline evoked response 402 shown in FIG. 4. Hence, processing facility 304 may determine that evoked response 602 is less than baseline evoked response 402. Evoked response 702 shown in FIG. 7 has an amplitude that is within a predetermined rage of the amplitude of baseline evoked response 402 shown in FIG. 4. Hence, processing facility 304 may determine that evoked response 702 is substantially the same as baseline evoked response 402.

Additionally or alternatively, processing facility 304 may compare different attributes of the baseline evoked response with the evoked response to determine whether the changes are due to either hair cells or neurons. For example, processing facility 304 may compare thresholds and/or slopes of the evoked response with the thresholds and/or slopes of the baseline evoked response and/or one or more other previously recorded evoked responses to determine whether there have been any changes.

If the evoked response (e.g., evoked responses 502 and 602) differs from the baseline evoked response (e.g., baseline evoked response 402) and/or the one or more previously recorded evoked responses (e.g., if the evoked response is not within a predetermined range of the baseline evoked response and/or the one or more previously recorded evoked responses), processing facility 304 may perform a predetermined action. In certain examples, the predetermined action may comprise setting one or more control parameters associated with an acoustic stimulation functionality of EAS sound processor 102 (e.g., by increasing an amplitude and/or intensity level of the acoustic stimulation provided by EAS system 100 and/or adjusting one or more other characteristics of the acoustic stimulation).

For example, based on the comparison between the evoked response and the baseline evoked response, EAS sound processor 102 (e.g., through processing facility 304) may perform the predetermined action by determining a degree of amplification to be used for future acoustic stimulation to be provided by EAS system 100 when EAS sound processor 102 switches from the self-fitting mode to a normal stimulation mode.

In some examples, if the comparison indicates that the evoked response is greater than the baseline evoked response, EAS sound processor 102 may decrease the degree of amplification to be used for the future acoustic stimulation. To illustrate, the exemplary evoked response 502 shown in FIG. 5 is greater than baseline evoked response 402. Accordingly, in such a situation, the predetermined action may include EAS sound processor 102 reducing a degree of amplification to be used for future acoustic stimulation to compensate for the difference.

Alternatively, if the comparison indicates that the evoked response is less than the baseline evoked response, EAS sound processor 102 may increase the degree of amplification to be used for the future acoustic stimulation. To illustrate, the exemplary evoked response 602 shown in FIG. 6 is less than baseline evoked response 402. Accordingly, in such a situation, the predetermined action may include EAS sound processor 102 increasing the degree of amplification to be used for future acoustic stimulation to compensate for the difference.

If the comparison indicates that the evoked response is within a predetermined threshold of the baseline evoked response, EAS sound processor 102 may maintain the degree of amplification to be used for the future acoustic stimulation. To illustrate, the exemplary evoked response 702 shown in FIG. 7 may be considered as being within a predetermined range of baseline evoked response 402 due to their relatively close steady state amplitudes. Accordingly, in such a situation, the predetermined action may include EAS sound processor 102 not making any changes the degree of amplification to be used for future acoustic stimulation.

EAS sound processor 102 may additionally or alternatively use the evoked response to determine one or more optimal crossover frequencies associated with the patient. As used herein, a "crossover frequency" refers to a boundary frequency that separates frequencies represented to the patient by acoustic stimulation and frequencies represented to the patient by electrical stimulation. For example, based on the baseline evoked response, EAS sound processor 102 may determine that acoustic stimulation evokes robust hair cell and neural responses until 450 Hz. This frequency may therefore be designated as the crossover frequency (i.e., the apical-most electrode can start providing electrical stimulation around that frequency). However, EAS sound processor 102 may compare an evoked response recorded during the self-fitting mode to the baseline evoked response and determine that acoustic stimulation now evokes robust hair cell and neural responses only until 400 Hz. Accordingly, EAS sound processor 102 may designate 400 Hz as the crossover frequency instead of 450 Hz for future stimulation.

EAS sound processor 102 may additionally or alternatively perform the predetermined action by evaluating a change in a hearing status of the patient based on the comparison between the evoked response and the baseline evoked response (e.g., baseline evoked response 402). For example EAS sound processor 102 may evaluate a residual hearing status of the patient in accordance with an evoked response that occurs in response to acoustic stimulation provided by EAS system 100. A variety of different factors may affect a residual hearing status of a patient. For example, wax buildup in the ear, infection, sickness, patient age, and/or any other factor may temporarily and/or permanently affect a residual hearing status of the patient.

To evaluate the residual hearing status of the patient, EAS sound processor 102 may compare the evoked response to a baseline evoked response and determine, based on a comparison, that the patient's residual hearing is changing (e.g., deteriorating). In response, EAS sound processor 102 may automatically adjust one or more control parameters governing an operation of EAS system 100 (e.g., by increasing an amplitude and/or intensity level of stimulation being provided to the user), and/or take any other action as may serve a particular implementation.

In some examples, based on the residual hearing status as determined by EAS sound processor 102, a clinician or other user may decide to provide further treatment to the patient. For example, the clinician may decide to apply systemic steroids if a drop in residual hearing is detected.

EAS sound processor 102 may additionally or alternatively provide one or more notifications to the patient and/or another user in accordance with an evoked response that occurs in response to stimulation provided by EAS system 100.

For example, if an evoked response is not within a predetermined range of a baseline evoked response and/or one or more previously recorded evoked responses, EAS sound processor 102 may provide the patient and/or another user with a notification. The notification may be an audible alert (e.g., one or more beeps), a visible alert (e.g., a flashing of an LED), a text-based alert, and/or any other type of notification as may serve a particular implementation. The patient and/or other user may then take appropriate action.

In some examples, EAS sound processor 102 may determine that an evoked response does not occur in response to stimulation provided by EAS system 100. EAS sound processor 102 may accordingly notify the patient, automatically adjust one or more stimulation parameters, and/or perform one or more other actions as may serve a particular implementation.

For example, EAS sound processor 102 may determine that a compound action potential does not occur in response to stimulation provided by EAS system 100. This may be indicative of auditory neuropathy, and may affect how EAS system 100 is to be fitted to the patient (e.g., EAS system 100 may be programmed to provide only electrical stimulation if residual hearing is no longer of consequence to the patient).

After EAS sound processor 102 performs any one or more of the exemplary predetermined actions described herein, EAS sound processor 102 may enter a normal operation mode in which EAS sound processor 102 directs cochlear implant 104 to apply electrical stimulation representative of a first portion of audio content presented to the patient, and directs a receiver (e.g., receiver 110) to apply acoustic stimulation representative of a second portion of the audio content presented to the patient. After a period of time subsequent to EAS sound processor 102 performing the predetermined action, changes may have occurred that may negatively affect the acoustic functionality of EAS system 100. Accordingly, in certain examples, EAS sound processor 102 may switch from the normal stimulation mode back to the self-fitting mode. EAS sound processor 102 may switch back to the self-fitting mode as often as necessary to facilitate optimal functionality of EAS system 100.

While switched back to the self-fitting mode, EAS sound processor 102 may direct the receiver to apply additional acoustic stimulation to the patient. In certain examples, the additional acoustic stimulation may include the same acoustic stimulation applied by the receiver while EAS sound processor 102 was in a previous self-fitting mode. EAS sound processor 102 may then record, using at least one electrode (e.g., electrode 108), an additional evoked response that occurs in response to the additional acoustic stimulation, compare the additional evoked response to the evoked response, and perform an additional predetermined action based on the comparison between the additional evoked response and the evoked response in any suitable manner, such as described herein.

As an example, a patient may get an infection that negatively affects the patient's residual hearing. EAS sound processor 102 may detect this deterioration in the patient's residual hearing by entering the self-fitting mode and comparing an evoked response with a baseline evoked response. EAS sound processor 102 may then perform a predetermined action by increasing an intensity level of the acoustic stimulation being provided by way of receiver 110. Subsequently, the infection may go away. EAS sound processor 102 may detect this by switching back to the self-fitting mode and comparing an additional evoked response recorded while in the self-fitting mode with the previous evoked response and/or the baseline evoked response. In response, the intensity level of the acoustic stimulation may be set (e.g., decreased) to the level it was prior to the infection. In this regard, EAS sound processor 102 may dynamically self-fit EAS system 100 to the patient as various changes may occur.

Figure 8:
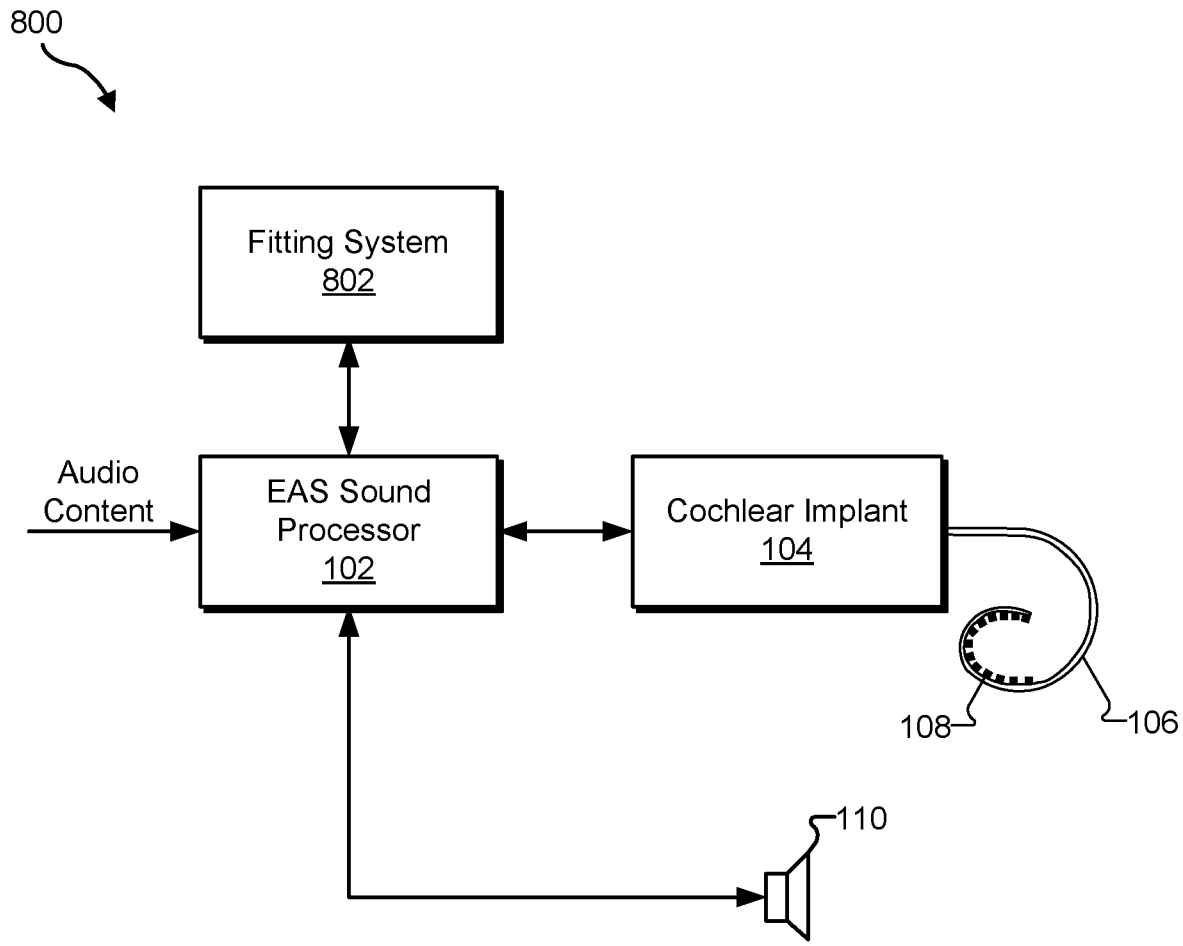
FIG. 8 shows an exemplary configuration in which the EAS system of FIG. 1 is communicatively coupled to an EAS sound processor according to principles described herein.

In certain examples, a fitting system may direct EAS sound processor 102 to enter the self-fitting mode. To illustrate, FIG. 8 shows an exemplary configuration 800 in which a fitting system 802 is communicatively coupled to EAS sound processor 102. Fitting system 802 may be communicatively coupled to EAS sound processor 102 in any suitable manner (e.g., through a wired or a wireless connection) and through any suitable communication platforms or technologies. Fitting system 802 may implemented by any suitable combination of computing and communication devices including, but not limited to, a fitting station, a personal computer, a laptop computer, a handheld device, a mobile device (e.g., a mobile phone), and/or any other suitable component as may serve a particular implementation. In some examples, fitting system 802 may provide one or more graphical user interfaces ("GUIs") with which a clinician or other user may interface in order to fit EAS system 100 to the patient and/or direct EAS processor 102 to perform any of the operation described herein.

In certain examples, fitting system 802 may direct EAS sound processor 102 to enter the self-fitting mode during an initial fitting procedure in which EAS system 100 is initially fit to the patient. Afterwards, and during a normal stimulation mode of EAS sound processor 102, fitting system 802 may periodically direct EAS sound processor 102 to enter the self-fitting mode to determine whether any changes have occurred with respect to the acoustic stimulation functionality of EAS system 100.

Figure 9:
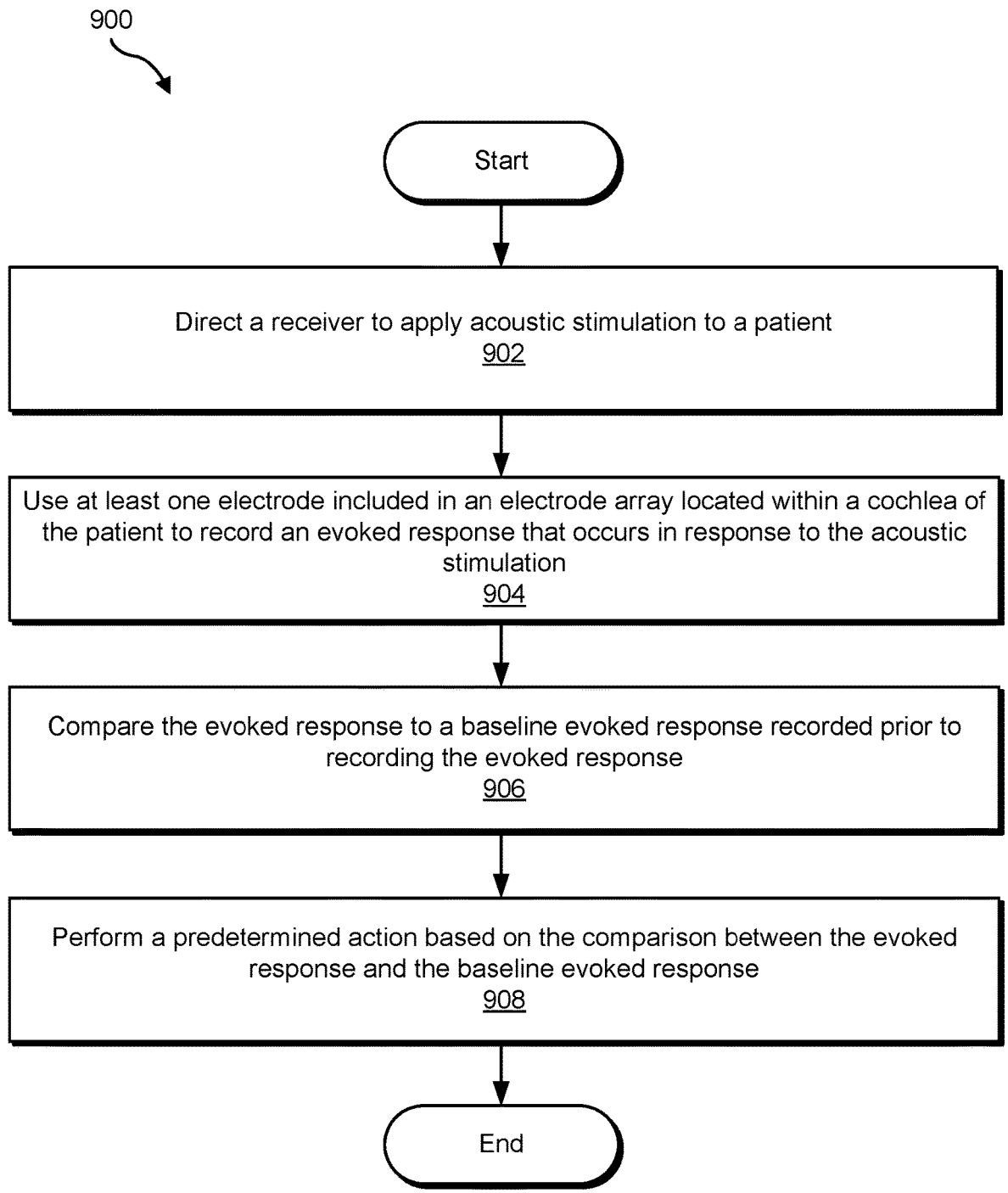
FIG. 9 illustrates an exemplary method according to principles described herein.

FIG. 9 illustrates an exemplary method 900. While FIG. 9 illustrates exemplary steps according to one embodiment, other embodiments may omit, add to, reorder, and/or modify any of the steps shown in FIG. 9. One or more of the steps shown in FIG. 9 may be performed by an EAS sound processor (e.g., EAS sound processor 102) and/or any implementation thereof.

In step 902, an EAS sound processor directs a receiver to apply acoustic stimulation to a patient. In certain examples, the acoustic stimulation may be provided while the EAS sound processor is in a self-fitting mode. Step 902 may be performed in any of the ways described herein.

In step 904, the EAS sound processor uses at least one electrode included in an electrode array located within a cochlea of the patient to record an evoked response that occurs in response to the acoustic stimulation. Step 904 may be performed in any of the ways described herein.

In step 906, the EAS sound processor compares the evoked response to a baseline evoked response recorded prior to recording the evoked response. Step 906 may be performed in any of the ways described herein.

In step 908, the EAS sound processor performs a predetermined action based on the comparison between the evoked response and the baseline evoked response.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a CD-ROM, DVD, any other optical medium, a RAM, a PROM, an EPROM, a FLASH-EEPROM, any other memory chip or cartridge, or any other tangible medium from which a computer can read.

Figure 10:
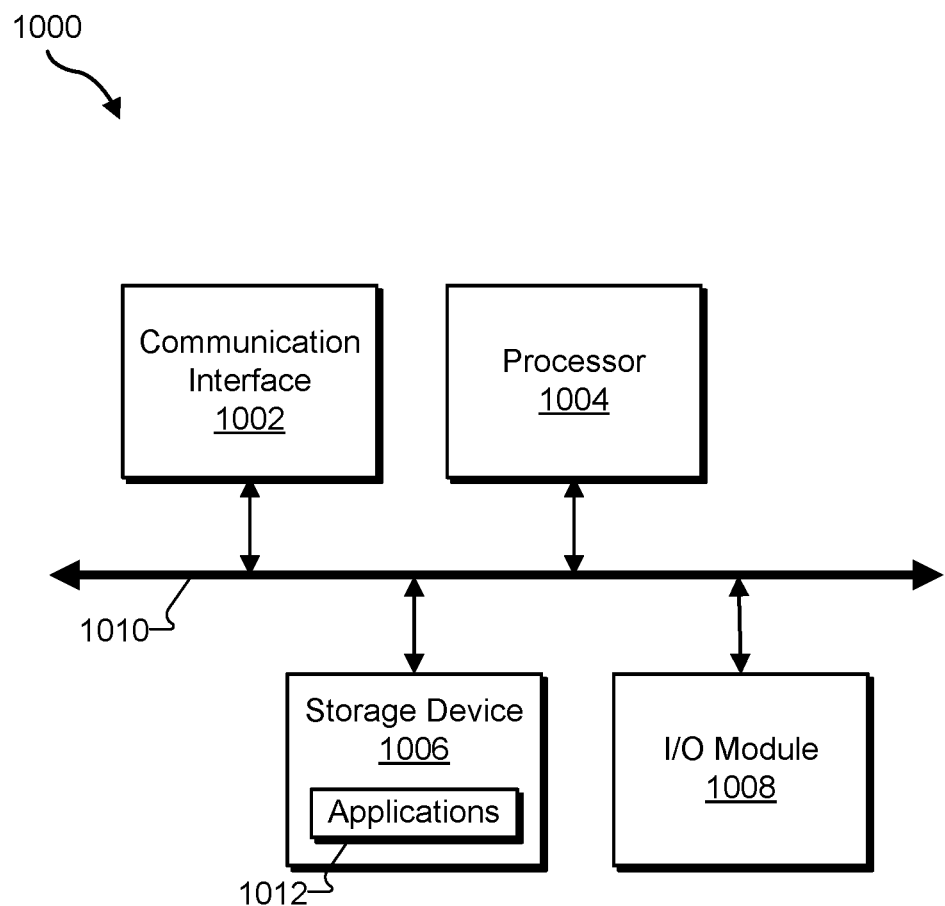
FIG. 10 illustrates an exemplary computing device according to principles described herein.

FIG. 10 illustrates an exemplary computing device 1000 that may be configured to perform one or more of the processes described herein. As shown in FIG. 10, computing device 1000 may include a communication interface 1002, a processor 1004, a storage device 1006, and an input/output ("I/O") module 1008 communicatively connected via a communication infrastructure 1010. While an exemplary computing device 1000 is shown in FIG. 10, the components illustrated in FIG. 10 are not intended to be limiting. Additional or alternative components may be used in other embodiments. Components of computing device 1000 shown in FIG. 10 will now be described in additional detail.

Communication interface 1002 may be configured to communicate with one or more computing devices. Examples of communication interface 1002 include, without limitation, a wired network interface (such as a network interface card), a wireless network interface (such as a wireless network interface card), a modem, an audio/video connection, and any other suitable interface.

Processor 1004 generally represents any type or form of processing unit capable of processing data or interpreting, executing, and/or directing execution of one or more of the instructions, processes, and/or operations described herein.

Processor 1004 may direct execution of operations in accordance with one or more applications 1012 or other computer-executable instructions such as may be stored in storage device 1006 or another computer-readable medium.

Storage device 1006 may include one or more data storage media, devices, or configurations and may employ any type, form, and combination of data storage media and/or device. For example, storage device 1006 may include, but is not limited to, a hard drive, network drive, flash drive, magnetic disc, optical disc, random access memory ("RAM"), dynamic RAM ("DRAM"), other non-volatile and/or volatile data storage units, or a combination or sub-combination thereof. Electronic data, including data described herein, may be temporarily and/or permanently stored in storage device 1006. For example, data representative of one or more executable applications 1012 configured to direct processor 1004 to perform any of the operations described herein may be stored within storage device 1006. In some examples, data may be arranged in one or more databases residing within storage device 1006.

I/O module 1008 may be configured to receive user input and provide user output and may include any hardware, firmware, software, or combination thereof supportive of input and output capabilities. For example, I/O module 1008 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1008 may include one or more devices for presenting output to a user, including, but not limited to, a graphics engine, a display (e.g., a display screen, one or more output drivers (e.g., display drivers), one or more audio speakers, and one or more audio drivers. In certain embodiments, I/O module 1008 is configured to provide graphical data to a display for presentation to a user. The graphical data may be representative of one or more graphical user interfaces and/or any other graphical content as may serve a particular implementation.

In some examples, any of the facilities and/or systems described herein may be implemented by or within one or more components of computing device 1000. For example, one or more applications 1012 residing within storage device 1006 may be configured to direct processor 1004 to perform one or more processes or functions associated with any of the facilities and/or systems described herein.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
    an electro-acoustic stimulation ("EAS") sound processor configured to be located external to a patient;
    a cochlear implant communicatively coupled to the EAS sound processor and configured to be implanted within the patient;
    wherein the EAS sound processor
        enters a self-fitting mode in which the EAS sound processor does not direct a receiver to apply, to the patient, acoustic stimulation representative of audio signals presented to the patient,
        directs, while in the self-fitting mode, the receiver to apply acoustic stimulation to the patient, the acoustic stimulation not representative of an audio signal presented to the patient,
        records, using at least one electrode configured to be located within a cochlea of the patient, an evoked response that occurs in response to the acoustic stimulation applied while the EAS sound processor is in the self-fitting mode,
        compares the evoked response to a baseline evoked response recorded by the EAS sound processor prior to recording the evoked response, and
        performs a predetermined action based on the comparison between the evoked response and the baseline evoked response.

2. The system of claim 1, wherein the predetermined action comprises setting one or more control parameters associated with an acoustic stimulation functionality of the EAS sound processor.

3. The system of claim 1, wherein the EAS sound processor performs the predetermined action by determining, based on the comparison between the evoked response and the baseline evoked response, a degree of amplification to be used for future acoustic stimulation to be provided by the system when the EAS sound processor switches from the self-fitting mode to a normal stimulation mode in which the EAS sound processor processes audio signals presented to the patient and directs the cochlear implant and/or the receiver to apply, to the patient, electrical and/or acoustic stimulation representative of the audio signals processed by the EAS sound processor.

4. The system of claim 3, wherein the EAS sound processor increases the degree of amplification to be used for the future acoustic stimulation if the comparison indicates that the evoked response is less than the baseline evoked response.

5. The system of claim 3, wherein the EAS sound processor decreases the degree of amplification to be used for the future acoustic stimulation if the comparison indicates that the evoked response is greater than the baseline evoked response.

6. The system of claim 3, wherein the EAS sound processor maintains the degree of amplification to be used for the future acoustic stimulation if the comparison indicates that the evoked response is within a predetermined threshold of the baseline evoked response.

7. The system of claim 1, wherein the EAS sound processor performs the predetermined action by using the comparison to determine an optimal crossover frequency associated with the patient.

8. The system of claim 1, wherein the EAS sound processor performs the predetermined action by evaluating a change in a hearing status of the patient based on the comparison between the evoked response and the baseline evoked response.

9. The system of claim 1, wherein the EAS sound processor switches, subsequent to performing the predetermined action, from the self-fitting mode to a normal stimulation mode during which the EAS sound processor:
    directs the cochlear implant to apply electrical stimulation representative of a first portion of audio content presented to the patient while the EAS sound processor is in the normal stimulation mode; and
    directs the receiver to apply acoustic stimulation representative of a second portion of the audio content presented to the patient while the EAS sound processor is in the normal stimulation mode.

10. The system of claim 9, wherein the EAS sound processor:
   switches from the normal stimulation mode back to the self-fitting mode;
   directs, while in the self-fitting mode, the receiver to apply additional acoustic stimulation to the patient;
   records, using the at least one electrode, an additional evoked response that occurs in response to the additional acoustic stimulation;
   compares the additional evoked response to the evoked response; and
   performs an additional predetermined action based on the comparison between the additional evoked response and the evoked response.

11. The system of claim 10, wherein the EAS sound processor performs the additional predetermined action by determining, based on the comparison between the additional evoked response and the evoked response, a degree of amplification to be used for future acoustic stimulation to be provided by the system when the EAS sound processor again switches from the self-fitting mode to the normal stimulation mode.

12. The system of claim 1, wherein the evoked response comprises at least one of an intracochlear hair-cell response, a cochlear microphonics response, an auditory nerve neurophonics response, and a neural response.

13. The system of claim 1, further comprising a fitting system that directs the EAS sound processor to enter the self-fitting mode.

14. The system of claim 1, wherein, while in the self-fitting mode, the EAS sound processor does not direct the cochlear implant to apply, to the patient, electrical stimulation representative of the audio signals presented to the patient.

15. An electro-acoustic stimulation ("EAS") sound processor included in an EAS system associated with a patient, the system further including a cochlear implant communicatively coupled to the EAS sound processor and configured to be implanted within the patient and a receiver communicatively coupled to the EAS sound processor and configured to be in communication with an ear of the patient, the EAS sound processor comprising:
   a stimulation management facility configured to
      enter a self-fitting mode in which the stimulation management facility does not direct the receiver to apply, to the patient, acoustic stimulation representative of audio signals presented to the patient, and
      direct, while in the self-fitting mode, the receiver to apply acoustic stimulation to the patient, the acoustic stimulation not representative of an audio signal presented to the patient; and
   a processing facility configured to
      record, using at least one electrode configured to be located within a cochlea of the patient, an evoked response that occurs in response to the acoustic stimulation applied while the stimulation management facility is in the self-fitting mode,
      compare the evoked response to a baseline evoked response recorded by the processing facility prior to recording the evoked response, and
      perform a predetermined action based on the comparison between the evoked response and the baseline evoked response.

16. The EAS sound processor of claim 15, wherein:
   the stimulation management facility is further configured to:
      switch, subsequent to performing the predetermined action, from the self-fitting mode to a normal stimulation mode;
      direct the cochlear implant to apply electrical stimulation representative of a first portion of audio content presented to the patient while the EAS sound processor is in the normal stimulation mode; and
      direct the receiver to apply acoustic stimulation representative of a second portion of the audio content presented to the patient while the EAS sound processor is in the normal stimulation mode.

17. The EAS sound processor of claim 16, wherein:
   the stimulation management facility is further configured to:
      switch from the normal stimulation mode back to the self-fitting mode; and
      direct, while in the self-fitting mode, the receiver to apply additional acoustic stimulation; and
   the processing facility is further configured to:
      record, using the at least one electrode, an additional evoked response that occurs in response to the additional acoustic stimulation;
      compare the additional evoked response to the evoked response; and
      perform an additional predetermined action based on the comparison between the additional evoked response and the evoked response.

18. The EAS sound processor of claim 15, wherein, while in the self-fitting mode, the stimulation management facility does not direct the cochlear implant to apply, to the patient, electrical stimulation representative of the audio signals presented to the patient.

19. A method comprising:
   entering, by an electro-acoustic stimulation ("EAS") sound processor communicatively coupled to a cochlear implant configured to be implanted within a patient and a receiver configured to be in communication with an ear of the patient, a self-fitting mode in which the EAS sound processor does not direct the receiver to apply, to the patient, acoustic stimulation representative of audio signals presented to the patient;
   directing, by the EAS sound processor while in the self-fitting mode, a receiver to apply acoustic stimulation to the patient, the acoustic stimulation not representative of an audio signal presented to the patient;
   using, by the EAS sound processor, at least one electrode configured to be located within a cochlea of the patient to record an evoked response that occurs in response to the acoustic stimulation applied while the EAS sound processor is in the self-fitting mode;
   comparing, by the EAS sound processor, the evoked response to a baseline evoked response recorded by the EAS sound processor prior to recording the evoked response; and
   performing, by the EAS sound processor, a predetermined action based on the comparison between the evoked response and the baseline evoked response.

20. The method of claim 19, wherein, while in the self-fitting mode, the EAS sound processor does not direct the cochlear implant to apply, to the patient, electrical stimulation representative of the audio signals presented to the patient.

* * * * *